United States Patent
Andriola et al.

(10) Patent No.: US 11,622,695 B1
(45) Date of Patent: Apr. 11, 2023

(54) INTRACARDIAC SENSORS WITH SWITCHABLE CONFIGURATIONS AND ASSOCIATED SYSTEMS AND METHODS

(71) Applicant: Shifamed Holdings, LLC, Campbell, CA (US)

(72) Inventors: Peter Andriola, Castro Valley, CA (US); Brian Fahey, Menlo Park, CA (US); Scott Robertson, Portland, OR (US); Anthony Pantages, San Jose, CA (US); Miles Alexander, Fremont, CA (US); William Jason Fox, San Mateo, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/916,412

(22) PCT Filed: Apr. 23, 2021

(86) PCT No.: PCT/US2021/028926
§ 371 (c)(1),
(2) Date: Sep. 30, 2022

(87) PCT Pub. No.: WO2021/217055
PCT Pub. Date: Oct. 28, 2021

Related U.S. Application Data

(60) Provisional application No. 63/014,327, filed on Apr. 23, 2020.

(51) Int. Cl.
*A61B 5/0215* (2006.01)
*A61B 5/00* (2006.01)

(52) U.S. Cl.
CPC .......... *A61B 5/0215* (2013.01); *A61B 5/6847* (2013.01); *A61B 5/6869* (2013.01);
(Continued)

(58) Field of Classification Search
CPC .......... A61B 5/0215–02158; A61B 2560/0276
See application file for complete search history.

(56) References Cited

U.S. PATENT DOCUMENTS

| 5,197,978 A | 3/1993 | Hess |
| 5,611,338 A | 3/1997 | Gallup et al. |

(Continued)

FOREIGN PATENT DOCUMENTS

| AU | 2005211243 | 8/2005 |
| AU | 2010344182 | 8/2012 |

(Continued)

OTHER PUBLICATIONS

Jodi Perkins, "Corvia Medical and physiQ Partner in Global Phase 3 Heart Failure Clinical Trial to Leverage Novel Digital Endpoints," Press Release, 2019 Copyright, Medical Alley Association, 3 pages.

(Continued)

*Primary Examiner* — Meredith Weare
(74) *Attorney, Agent, or Firm* — Perkins Coie LLP

(57) ABSTRACT

The present technology relates to intracardiac sensors and associated systems and methods. In some embodiments, the present technology includes a device for monitoring pressure within a patient's heart. The device can include an implantable capacitor having a capacitance value that is variable based on the pressure within the patients heart and a sensing circuit configured to measure the capacitance value. The device can also include an implantable inductor and a power circuit configured to wirelessly receive power from an external source via the inductor. When the device is in a first configuration, the capacitor can be electrically coupled to the sensing circuit and the inductor can be electrically coupled to the power circuit. When the device is in a second configuration, the capacitor can be electrically coupled to the inductor to form a resonant circuit.

22 Claims, 4 Drawing Sheets

(52) U.S. Cl.
CPC .......... *A61B 2560/0219* (2013.01); *A61B 2560/0276* (2013.01); *A61B 2562/0247* (2013.01)

(56) References Cited

U.S. PATENT DOCUMENTS

| | | | |
|---|---|---|---|
| 6,077,298 A | 6/2000 | Tu et al. | |
| 6,120,534 A | 9/2000 | Ruiz | |
| 6,165,209 A | 12/2000 | Patterson et al. | |
| 6,240,322 B1 | 5/2001 | Peterfeso et al. | |
| 6,783,499 B2 | 8/2004 | Schwartz | |
| 6,909,920 B2 | 6/2005 | Lokhoff et al. | |
| 6,926,670 B2 * | 8/2005 | Rich .................. A61B 5/6882 600/459 | |
| 7,524,329 B2 | 4/2009 | Rucker | |
| 7,617,001 B2 | 11/2009 | Penner et al. | |
| 7,634,318 B2 | 12/2009 | Tran et al. | |
| 7,658,747 B2 | 2/2010 | Forde et al. | |
| 7,860,579 B2 | 12/2010 | Goetzinger et al. | |
| 8,043,360 B2 | 10/2011 | McNamara et al. | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,235,933 B2 | 8/2012 | Keren et al. | |
| 8,252,042 B2 | 8/2012 | McNamara et al. | |
| 8,328,751 B2 | 12/2012 | Keren et al. | |
| 8,460,372 B2 | 6/2013 | McNamara et al. | |
| 8,696,611 B2 | 4/2014 | Nitzan et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,882,697 B2 | 11/2014 | Celermajer et al. | |
| 8,951,223 B2 | 2/2015 | McNamara et al. | |
| 9,005,155 B2 | 4/2015 | Sugimoto | |
| 9,034,034 B2 | 5/2015 | Nitzan et al. | |
| 9,204,842 B2 | 12/2015 | Mothilal et al. | |
| 9,205,236 B2 | 12/2015 | McNamara et al. | |
| 9,232,997 B2 | 1/2016 | Sugimoto et al. | |
| 9,277,995 B2 | 3/2016 | Celermajer et al. | |
| 9,358,371 B2 | 6/2016 | McNamara et al. | |
| 9,456,812 B2 | 10/2016 | Finch et al. | |
| 9,610,041 B2 | 4/2017 | Foster et al. | |
| 9,629,715 B2 | 4/2017 | Nitzan et al. | |
| 9,642,993 B2 | 5/2017 | McNamara et al. | |
| 9,649,480 B2 | 5/2017 | Sugimoto et al. | |
| 9,681,948 B2 | 6/2017 | Levi et al. | |
| 9,707,382 B2 | 7/2017 | Nitzan et al. | |
| 9,713,696 B2 | 7/2017 | Yacoby et al. | |
| 9,724,499 B2 | 8/2017 | Rottenberg et al. | |
| 9,757,107 B2 | 9/2017 | McNamara et al. | |
| 9,775,636 B2 | 10/2017 | Fazio et al. | |
| 9,918,856 B2 | 3/2018 | Favier et al. | |
| 9,937,036 B2 | 4/2018 | Sugimoto et al. | |
| 9,943,670 B2 | 4/2018 | Keren et al. | |
| 9,980,815 B2 | 5/2018 | Nitzan et al. | |
| 10,045,766 B2 | 8/2018 | McNamara et al. | |
| 10,076,403 B1 | 9/2018 | Eigler et al. | |
| 10,188,375 B2 | 1/2019 | McNamara et al. | |
| 10,207,087 B2 | 2/2019 | Keren | |
| 10,251,740 B2 | 4/2019 | Eigler et al. | |
| 10,292,690 B2 | 5/2019 | Celermajer et al. | |
| 10,350,384 B2 | 7/2019 | Farnan et al. | |
| 10,357,357 B2 | 7/2019 | Levi et al. | |
| 10,368,981 B2 | 8/2019 | Nitzan et al. | |
| 10,376,680 B2 | 8/2019 | McNamara et al. | |
| 10,398,421 B2 | 9/2019 | Celermajer | |
| 10,405,903 B1 | 9/2019 | Biesinger et al. | |
| 10,413,284 B2 | 9/2019 | McNamara et al. | |
| 10,413,286 B2 | 9/2019 | McNamara et al. | |
| 10,463,477 B2 | 11/2019 | Forcucci et al. | |
| 10,463,490 B2 | 11/2019 | Rottenberg et al. | |
| 10,471,251 B1 | 11/2019 | Manicka | |
| 10,478,594 B2 | 11/2019 | Yacoby et al. | |
| 10,568,751 B2 | 2/2020 | McNamara | |
| 10,588,611 B2 | 3/2020 | Magnin et al. | |
| 10,610,210 B2 | 4/2020 | Finch et al. | |
| 10,624,621 B2 | 4/2020 | Celermajer | |
| 10,632,292 B2 | 4/2020 | Forcucci et al. | |
| 10,639,459 B2 | 5/2020 | Nitzan et al. | |
| 10,675,450 B2 | 6/2020 | Finch | |
| 10,828,151 B2 | 11/2020 | Nitzan et al. | |
| 10,835,394 B2 | 11/2020 | Nae et al. | |
| 10,898,698 B1 | 1/2021 | Eigler et al. | |
| 10,912,645 B2 | 2/2021 | Rottenberg et al. | |
| 10,925,706 B2 | 2/2021 | Eigler et al. | |
| 10,932,786 B2 | 3/2021 | McNamara et al. | |
| 10,940,296 B2 | 3/2021 | Keren | |
| 10,945,716 B2 | 3/2021 | Chen et al. | |
| 11,135,410 B2 | 10/2021 | Finch et al. | |
| 2002/0072656 A1 | 6/2002 | Vantassel et al. | |
| 2002/0161427 A1 | 10/2002 | Rabkin et al. | |
| 2002/0177891 A1 | 11/2002 | Miles et al. | |
| 2003/0127090 A1 | 7/2003 | Gifford et al. | |
| 2003/0163190 A1 | 8/2003 | LaFont et al. | |
| 2004/0158143 A1 | 8/2004 | Flaherty et al. | |
| 2004/0186566 A1 | 9/2004 | Hindrichs et al. | |
| 2005/0060030 A1 | 3/2005 | Lashinski et al. | |
| 2005/0101946 A1 | 5/2005 | Govari et al. | |
| 2005/0148925 A1 | 7/2005 | Rottenberg et al. | |
| 2005/0204811 A1 | 9/2005 | Neff | |
| 2005/0288722 A1 | 12/2005 | Eigler et al. | |
| 2006/0009810 A1 | 1/2006 | Mann et al. | |
| 2006/0047205 A1 | 3/2006 | Ludomirsky et al. | |
| 2006/0116625 A1 | 6/2006 | Renati et al. | |
| 2006/0200030 A1 | 9/2006 | White et al. | |
| 2007/0010837 A1 | 1/2007 | Tanaka | |
| 2007/0088220 A1 | 4/2007 | Stahmann | |
| 2007/0088223 A1 | 4/2007 | Mann et al. | |
| 2007/0118039 A1 | 5/2007 | Bodecker et al. | |
| 2007/0150019 A1 | 6/2007 | Youker et al. | |
| 2007/0282157 A1 | 12/2007 | Rottenberg et al. | |
| 2008/0033527 A1 | 2/2008 | Nunez et al. | |
| 2008/0097276 A1 | 4/2008 | Bertrand et al. | |
| 2008/0108904 A1 | 5/2008 | Heil | |
| 2008/0119891 A1 | 5/2008 | Miles et al. | |
| 2008/0127689 A1 | 6/2008 | McCusker et al. | |
| 2008/0171941 A1 | 7/2008 | Huelskamp et al. | |
| 2008/0208083 A1 | 8/2008 | Lin et al. | |
| 2009/0036975 A1 | 2/2009 | Ward et al. | |
| 2009/0243956 A1 | 10/2009 | Keilman et al. | |
| 2009/0270742 A1 | 10/2009 | Wolinsky et al. | |
| 2009/0281597 A1 | 11/2009 | Parramon et al. | |
| 2010/0063375 A1 | 3/2010 | Kassab et al. | |
| 2010/0076366 A1 | 3/2010 | Henderson, Sr. et al. | |
| 2010/0076517 A1 | 3/2010 | Imran | |
| 2010/0106028 A1 | 4/2010 | Penner et al. | |
| 2010/0168672 A1 | 7/2010 | Carr | |
| 2010/0179449 A1 | 7/2010 | Chow et al. | |
| 2010/0241241 A1 | 9/2010 | McKnight et al. | |
| 2010/0249560 A1 | 9/2010 | Levinson et al. | |
| 2010/0262021 A1 | 10/2010 | Yadav et al. | |
| 2010/0262036 A1 | 10/2010 | Najafi et al. | |
| 2010/0275592 A1 | 11/2010 | Topliss et al. | |
| 2010/0298930 A1 | 11/2010 | Orlov | |
| 2011/0082377 A1 | 4/2011 | Mahajau et al. | |
| 2011/0218480 A1 | 9/2011 | Rottenberg et al. | |
| 2011/0218481 A1 | 9/2011 | Rottenberg et al. | |
| 2011/0257723 A1 | 10/2011 | McNamara | |
| 2011/0264194 A1 | 10/2011 | Griswold | |
| 2011/0282217 A1 | 11/2011 | Nashet | |
| 2011/0295183 A1 | 12/2011 | Finch et al. | |
| 2012/0265296 A1 | 10/2012 | McNamara et al. | |
| 2012/0290062 A1 | 11/2012 | McNamara et al. | |
| 2013/0123569 A1 | 5/2013 | Gross | |
| 2013/0144379 A1 | 6/2013 | Najafi et al. | |
| 2013/0178783 A1 | 7/2013 | McNamara et al. | |
| 2013/0178784 A1 | 7/2013 | McNamara et al. | |
| 2013/0192611 A1 | 8/2013 | Taepke, II et al. | |
| 2013/0197423 A1 | 8/2013 | Keren et al. | |
| 2013/0211221 A1 | 8/2013 | Sunnarborg et al. | |
| 2013/0253343 A1 | 9/2013 | Waldhauser et al. | |
| 2013/0261531 A1 | 10/2013 | Gallagher et al. | |
| 2014/0012342 A1 | 1/2014 | Penner et al. | |

(56) References Cited

U.S. PATENT DOCUMENTS

| | | |
|---|---|---|
| 2014/0046427 A1 | 2/2014 | Michalak |
| 2014/0128795 A1 | 5/2014 | Karen et al. |
| 2014/0128796 A1 | 5/2014 | Keren et al. |
| 2014/0135647 A1 | 5/2014 | Wolf, II |
| 2014/0163449 A1 | 6/2014 | Rottenberg et al. |
| 2014/0213959 A1 | 7/2014 | Nitzan et al. |
| 2014/0222040 A1 | 8/2014 | Park et al. |
| 2014/0277054 A1 | 9/2014 | McNamara et al. |
| 2014/0306807 A1 | 10/2014 | Rowland et al. |
| 2015/0034217 A1 | 2/2015 | Vad |
| 2015/0119796 A1 | 4/2015 | Finch |
| 2015/0148731 A1 | 5/2015 | McNamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph |
| 2015/0230843 A1 | 8/2015 | Palmer et al. |
| 2015/0231387 A1* | 8/2015 | Harding ............ A61B 5/4836 600/393 |
| 2016/0022423 A1 | 1/2016 | McNamara et al. |
| 2016/0151179 A1 | 6/2016 | Favier et al. |
| 2016/0158561 A1 | 6/2016 | Reddy |
| 2016/0235999 A1 | 8/2016 | Nuta et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0168463 A1 | 6/2018 | Morris et al. |
| 2018/0256865 A1 | 9/2018 | Finch et al. |
| 2018/0262037 A1 | 9/2018 | Meskeus |
| 2018/0310839 A1 | 11/2018 | McCaffrey et al. |
| 2019/0000327 A1 | 1/2019 | Doan et al. |
| 2019/0014993 A1 | 1/2019 | Kaiser |
| 2019/0015103 A1 | 1/2019 | Sharma |
| 2019/0021861 A1 | 1/2019 | Finch |
| 2019/0150758 A1 | 5/2019 | Sailey et al. |
| 2019/0167197 A1 | 6/2019 | Abuuassar et al. |
| 2019/0173505 A1 | 6/2019 | Koyama |
| 2019/0175883 A1 | 6/2019 | Wessler et al. |
| 2019/0192864 A1 | 6/2019 | Koop et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0298556 A1 | 10/2019 | Bohn et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0188143 A1 | 6/2020 | McNamara |
| 2020/0196867 A1* | 6/2020 | Andersen ............ A61B 5/01 |
| 2020/0196876 A1 | 6/2020 | Minor et al. |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0261705 A1 | 8/2020 | Nitzan et al. |
| 2020/0268515 A1 | 8/2020 | Vettukattil et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2021/0059527 A1 | 3/2021 | Najafi |
| 2021/0085935 A1 | 3/2021 | Fahey et al. |
| 2021/0100665 A1 | 4/2021 | Nae et al. |
| 2021/0121179 A1 | 4/2021 | Ben-David et al. |
| 2021/0153776 A1 | 5/2021 | Minar et al. |
| 2021/0177508 A1 | 6/2021 | Kellerman |
| 2021/0205590 A1 | 7/2021 | Fahey et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0299425 A1 | 9/2021 | Kume et al. |
| 2021/0299430 A1 | 9/2021 | Ratz et al. |
| 2021/0361257 A1 | 11/2021 | Eimer et al. |
| 2021/0370032 A1 | 12/2021 | Fahey et al. |
| 2022/0039670 A1 | 2/2022 | Berrada et al. |
| 2022/0039671 A1 | 2/2022 | Fahey |
| 2022/0118228 A1 | 4/2022 | Fahey et al. |
| 2022/0142652 A1 | 5/2022 | Alexander et al. |
| 2022/0184355 A1 | 6/2022 | Fahey et al. |
| 2022/0226000 A1 | 7/2022 | Alexander et al. |
| 2022/0226623 A1 | 7/2022 | Fahey et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 2013CN06525 | 8/2014 |
| CN | 105662653 | 6/2016 |
| CN | 109646063 A | 4/2019 |
| CN | 110536657 | 12/2019 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |
| WO | WO2005074367 | 8/2005 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |

(56) References Cited

FOREIGN PATENT DOCUMENTS

| | | |
|---|---|---|
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2018024868 | 2/2018 |
| WO | WO2018132549 | 7/2018 |
| WO | WO2018158747 | 9/2018 |
| WO | WO2019186101 | 2/2019 |
| WO | WO2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021126699 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021224736 | 11/2021 |
| WO | WO2022046921 | 3/2022 |
| WO | WO2022076601 | 4/2022 |
| WO | WO2022081980 | 4/2022 |
| WO | WO2022103973 | 5/2022 |

OTHER PUBLICATIONS

Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.

International Search Report and Written Opinion received for International Application No. PCT/US19/69106 filed Dec. 31, 2019; Applicant: Shifamed Holdings, LLC; dated Mar. 23, 2020; 10 pages.

International Search Report and Written Opinion received for International Application No. PCT/US20/49996 filed Sep. 9, 2020; Applicant: Shifamed Holdings, LLC; dated Feb. 17, 2021; 16 pages.

International Search Report and Written Opinion received for International Application No. PCT/US20/063360 filed Dec. 4, 2020; Applicant: Shifamed Holdings, LLC; dated Apr. 5, 2021; 13 pages.

International Search Report and Written Opinion received for International Application No. PCT/US20/64529 filed Dec. 11, 2020; Applicant: Shifamed Holdings, LLC; dated Apr. 8, 2021; 12 pages.

International Search Report and Written Opinion received for International Application No. PCT/US19/68354, filed Dec. 23, 2019; Applicant: Shifamed Holdings, LLC; dated Mar. 17, 2020; 11 pages.

International Search Report and Written Opinion received for International Application No. PCT/US21/16932, filed Feb. 5, 2021; Applicant: Shifamed Holdings, LLC; dated Jun. 3, 2021; 11 pages.

International Search Report and Written Opinion received for International Application No. PCT/US21/14433, filed Jan. 21, 2021; Applicant: Shifamed Holdings, LLC; dated May 14, 2021; 16 pages.

International Search Report and Written Opinion received for International Application No. PCT/US21/28926, filed Apr. 23, 2021; Applicant: Shifamed Holdings, LLC; dated Jul. 22, 2021; 16 pages.

International Search Report and Written Opinion received for International Application No. PCT/US20/12059, filed Jan. 2, 2020; Applicant: Shifamed Holdings, LLC; dated Jun. 5, 2020; 12 pages.

International Search Report and Written Opinion received for International Application No. PCT/US20/25509, filed Mar. 27, 2020; Applicant: Shifamed Holdings, LLC; dated Jun. 25, 2020; 9 pages.

International Search Report and Written Opinion received for International Application No. PCT/US20/26738, filed Apr. 3, 2020; Applicant: Shifamed Holdings, LLC; dated Jun. 30, 2020; 8 pages.

International Search Report and Written Opinion received for International Application No. PCT/US21/28931, filed Apr. 23, 2021; Applicant: Shifamed Holdings, LLC; dated Sep. 24, 2021; 20 pages.

International Search Report and Written Opinion received for International Application No. PCT/US21/27747, filed Apr. 16, 2021; Applicant: Shifamed Holdings, LLC; dated Oct. 1, 2021; 16 pages.

International Search Report and Written Opinion received for International Application No. PCT/US21/53836, filed Oct. 6, 2021; Applicant: Shifamed Holdings, LLC; dated Jan. 25, 2022; 20 pages.

International Search Report and Written Opinion received for International Application No. PCT/US21/47573, filed Aug. 25, 2021; Applicant: Shifamed Holdings, LLC; dated Feb. 3, 2022; 15 pages.

Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, pp. 9, col. 1, In 5-6.

Hossain, M. et al. "In situ preparation of graphene-ZnO composites for enhanced graphite exfoliation and graphene-nylon-6 composite films," Journal of Applied Polymer Science, Dec. 5, 2016, vol. 134, No. 27, p. 8, In 15-16.

International Search Report and Written Opinion received for International Application No. PCT/US21/55191, filed Oct. 15, 2021; Applicant: Shifamed Holdings, LLC; dated Mar. 1, 2022; 12 pages.

Anomet Products "Conductive Nitinol Wire" Aug. 15, 2020 (Aug. 15, 2020) Retrieved from website <URL: https://helpx.adobe.com/acrobat/using/allow-or-block-links-internet.html?mv=product&mv2=acrobat>, 4 pages.

(56) References Cited

OTHER PUBLICATIONS

International Search Report and Written Opinion received for International Application No. PCT/US21/58996, filed Nov. 11, 2021; Applicant: Shifamed Holdings, LLC; dated Feb. 7, 2022; 23 pages.

* cited by examiner

INTRACARDIAC SENSORS WITH SWITCHABLE CONFIGURATIONS AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2021/028926, filed Apr. 23, 2021, which claims the benefit of U.S. Provisional Patent Application No. 63/014,327, filed Apr. 23, 2020, each of which is incorporated herein by reference in its entirety.

TECHNICAL FIELD

The present technology generally relates to implantable medical devices and, in various aspects, implantable devices for treating heart failure such as shunts, sensors, and associated systems and methods.

BACKGROUND

Implantable shunting systems are widely used to treat a variety of patient conditions by shunting fluid from a first body region/cavity to a second body region/cavity. The flow of fluid through the shunting systems is primarily controlled by the pressure gradient across the shunt lumen and the geometry (e.g., size) of the shunt lumen. One challenge with conventional shunting systems is selecting the appropriate geometry of the shunt lumen for a particular patient. A lumen that is too small may not provide enough therapy to the patient, while a lumen that is too large may create new issues in the patient. Despite this, most conventional shunts cannot be adjusted once they have been implanted. Accordingly, once the system is implanted, the therapy provided by the shunting system cannot be adjusted or titrated to meet the patient's individual needs.

As a result of the above, shunting systems with adjustable lumens have recently been proposed to provide a more personalized or titratable therapy. Such systems enable clinicians to titrate the therapy to an individual patient's needs, as well as adjust the therapy over time as the patient's disease changes. Adjustable shunting systems, however, generally require energy to drive the adjustment. Energy can be delivered invasively (e.g., energy delivered via a catheter) or non-invasively (e.g., energy delivered to an implanted battery via induction). The energy required to adjust the shunt varies depending on the actuation mechanism incorporated into the shunting system.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1:
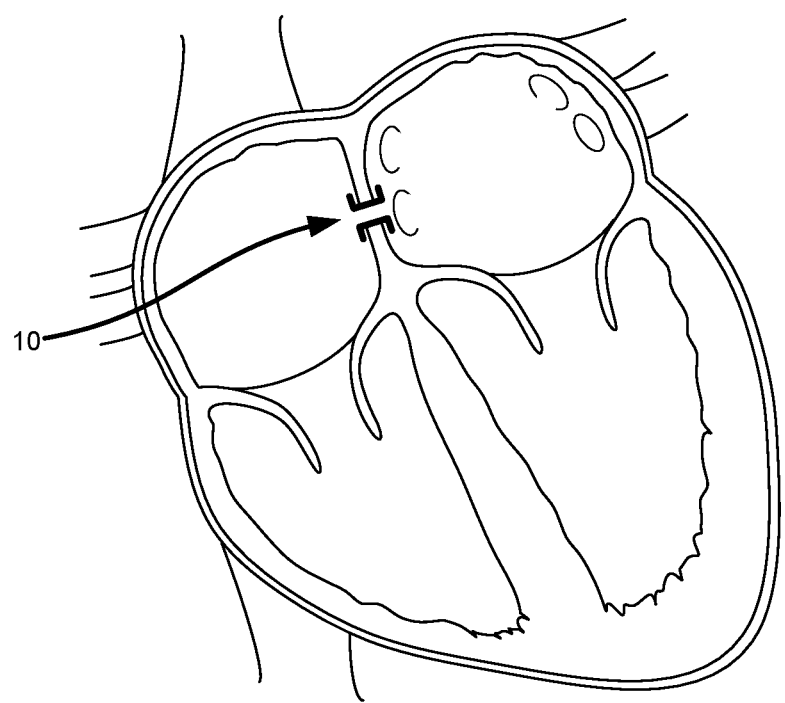
FIG. 1 is a schematic illustration of an interatrial device implanted in a heart and configured in accordance with an embodiment of the present technology.

The present technology is generally directed to devices for monitoring intracardiac pressure and/or other physiological parameters of a patient's heart. A device configured in accordance with an embodiment of the present technology can include, for example, an implantable capacitor having a capacitance value configured to vary based on the pressure within the patient's heart. The capacitor can be operably coupled to a sensing circuit configured to measure the capacitance value. The sensing circuit can measure the capacitance value continuously, intermittently, or at certain times (e.g., based on a triggering event). The device can also include an implantable inductor operably coupled to a power circuit configured to wirelessly receive power from an external source via the inductor. The power circuit can be electrically coupled to the sensing circuit to provide power thereto.

In some embodiments, the device includes a switching assembly that is changeable between a first configuration (e.g., an active sensing configuration) and a second configuration (e.g., a passive sensing configuration) to alter the electrical interconnections between the capacitor, sensing circuit, inductor, and power circuit. When the switching assembly is in the first configuration, the switching assembly can electrically couple the capacitor to the sensing circuit and electrically couple the inductor to the power circuit. As a result, the sensing circuit can be powered by the power circuit and can actively measure the capacitance value of the capacitor (e.g., to determine intracardiac pressure) using energy input from an implanted energy source. The switching assembly can be switched to the second configuration (e.g., in response to a failure in power transmission to the sensing circuit or other electronics failure) to electrically couple the capacitor to the inductor to form a resonant circuit. The resonant frequency of the resonant circuit can passively vary based on the capacitance value of the capacitor without any energy input from an implanted energy source. Accordingly, the resonant frequency—and therefore, the capacitance value of the capacitor—can subsequently be measured via an external device (e.g., to determine intracardiac pressure), even if the active electronics of the device are not functioning properly.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-4.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

As used herein, the terms "interatrial device," "interatrial shunt device," "IAD," "IASD," "interatrial shunt," and "shunt" are used interchangeably to refer to a device that, in at least one configuration, includes a shunting element that provides a blood flow between a first region (e.g., a LA of a heart) and a second region (e.g., a RA or coronary sinus of the heart) of a patient. Although described in terms of a shunt between the atria, namely the left and right atria, one will appreciate that the technology may be applied equally to devices positioned between other chambers and passages of the heart, or between other parts of the cardiovascular system. For example, any of the shunts described herein, including those referred to as "interatrial," may be nevertheless used and/or modified to shunt between the LA and the coronary sinus, or between the right pulmonary vein and the superior vena cava. Moreover, while the disclosure herein primarily describes shunting blood from the LA to the RA, the present technology can be readily adapted to shunt blood from the RA to the LA to treat certain conditions, such as pulmonary hypertension. For example, mirror images of embodiments, or in some cases identical embodiments, used to shunt blood from the LA to the RA can be used to shunt blood from the RA to the LA in certain patients.

Although certain embodiments herein are described in the context of capacitive pressure sensors, one of skill in the art will appreciate that the present technology can also be applied to other types of capacitive sensors for measuring other parameters of a patient's heart and/or an implanted shunting element, such as capacitive proximity sensors (e.g., to measure lumen diameter of an interatrial shunt). Alternatively or in combination, some embodiments herein can use other types of sensors, such as resistive or inductive sensors. Additionally, although certain embodiments herein are discussed as being part of an interatrial shunting system, one of skill in the art will appreciate that the present technology can be implemented in other types of systems for treating heart failure (e.g., systems that do not involve interatrial shunts), or can be used as a stand-alone device.

The headings provided herein are for convenience only and do not interpret the scope or meaning of the claimed present technology.

A. Interatrial Shunts for Treatment of Heart Failure

Heart failure can be classified into one of at least two categories based upon the ejection fraction a patient experiences: (1) HFpEF, historically referred to as diastolic heart failure or (2) HFrEF, historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Interatrial shunts have recently been proposed as a way to reduce elevated left atrial pressure, and this emerging class of cardiovascular therapeutic interventions has been demonstrated to have significant clinical promise. FIG. 1 shows the conventional placement of a shunt in the septal wall between the LA and RA. Most conventional interatrial shunts (e.g., shunt 10) involve creating a hole or inserting a structure with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right-heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With many such traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select the size—perioperatively or post-implant—based on the patient.

A further challenge with conventional interatrial shunts is that the function of the LA (and more generally, the cardiovascular system) can vary depending on a number of factors, for example during exercise, during periods where a patient's medication adherence has slipped, as the patient's disease progresses, or during other periods. Existing conventional shunts are generally static in nature and lack an ability to adapt to patient conditions in such a way to optimize therapy.

Other shortcomings of existing conventional interatrial shunts include: (1) shunts tending to be permanently implanted in the septal wall in a way that complicates or prevents future transseptal access, which may prohibit or complicate additional left-heart procedures that generally would require transseptal access; (2) shunts tending to be fixed and unable to adapt to changing patient conditions, such as progression of disease, and (3) a lack of sensors and/or machine-learning capability that limit the information available from the patient and limit the ability to improve therapy for the patient (or for the larger patient cohort) over time.

B. Select Embodiments of Intracardiac Monitoring Devices

As provided above, the present technology is generally directed to devices for monitoring intracardiac pressures and/or other parameters (e.g., physiologic parameters and/or parameters of an implanted shunt). These devices may be valuable as stand-alone devices or for use in an interatrial shunting system or another implanted treatment system for cardiovascular or other applications. Such devices can include an implantable capacitor (e.g., a capacitive pressure sensor) having a capacitance value configured to vary based on the pressure within the patient's heart. The capacitor can be operably coupled to a sensing circuit configured to measure the capacitance value. The device can also include an implantable inductor (e.g., a receiver coil) operably coupled to a power circuit configured to wirelessly receive power from an external source via the inductor. The power circuit can be electrically coupled to the sensing circuit to provide power thereto (e.g., directly or indirectly via an energy storage component such as a chargeable battery).

In some embodiments, the devices herein are switchable between a first configuration and a second configuration. The first configuration, for example, can be an active sensing configuration in which the sensing circuit receives power from the power circuit to actively measure the capacitance value of the capacitor and, optionally, determines intracardiac pressure based on the measured capacitance value. The second configuration can be a passive sensing configuration in which the capacitor and inductor are electrically coupled to form a resonant circuit (e.g., an LC circuit) having a resonant frequency that varies based, for example, on the capacitance value of the capacitor (which may vary depending on the pressure of the local environment). The resonant frequency can be measured using an external device (e.g., a device that applies an AC magnetic field) to determine the capacitance value and therefore the corresponding intracardiac pressure. In some embodiments, the devices herein are automatically switched between the first configuration and the second configuration if an electronics failure or malfunction occurs (e.g., a failure or malfunction in power transmission to the sensing circuit), thus permitting passive intracardiac pressure monitoring even if the active monitoring components of the device are no longer functioning properly. As a result, the present technology is expected to improve the flexibility and longevity of intracardiac pressure monitoring devices. In other embodiments, the switch between the first and second configurations can be reversible and/or temporary. For example, a user can instruct the device (e.g., via a signal sent to electronics within the device) to temporarily suspend operation of the first configuration (e.g., active sensing configuration) and enable functionality of the second configuration (e.g., passive sensing configuration). The device can subsequently revert to operation in the first configuration (e.g., upon completion of an operation, after a set time period, and/or based on other criteria).

Figure 2A:
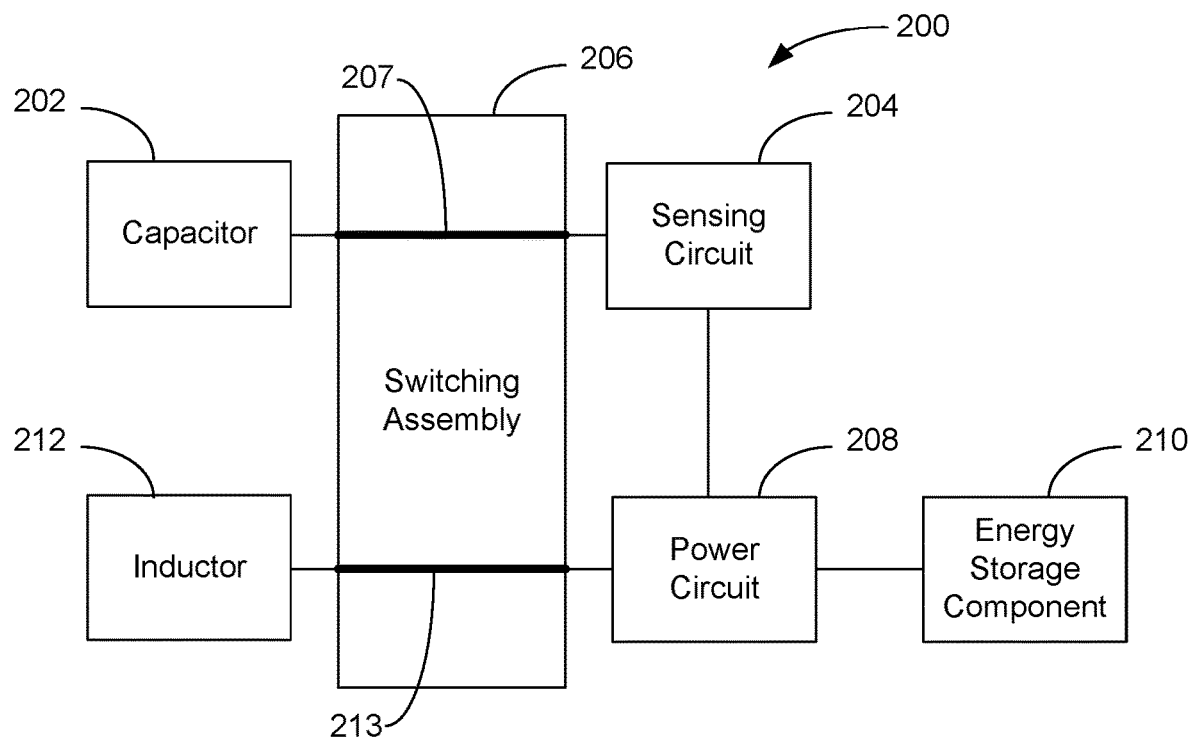
FIGS. 2A and 2B are schematic diagrams of an intracardiac monitoring device configured in accordance with an embodiment of the present technology.
Figure 2B:
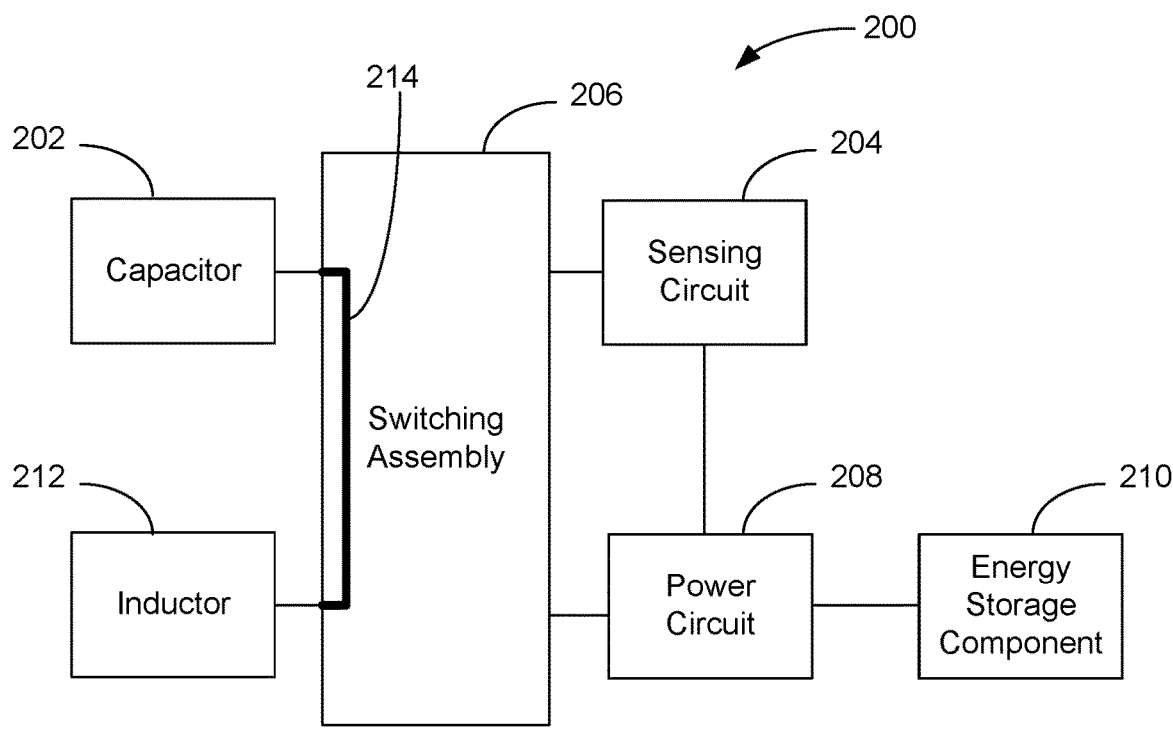

FIGS. 2A and 2B are schematic diagrams of an intracardiac monitoring device 200 configured in accordance with an embodiment of the present technology. More specifically, FIG. 2A illustrates the device 200 in a first configuration (e.g., an active sensing configuration) while FIG. 2B illustrates the device 200 in a second configuration (e.g., a passive sensing configuration). Referring first to FIG. 2A, the device 200 includes a capacitor 202 having a capacitance value C. The capacitor 202 can be configured to be implanted within a patient's heart (e.g., within the LA or RA and/or coupled to a septal wall, etc.—not shown). The capacitor 202 can be a variable capacitor such that the capacitance value C changes based on the operating conditions of the capacitor 202. In some embodiments, for example, the capacitor 202 is or is part of a capacitive intracardiac pressure sensor (not shown) such that when the sensor is implanted in the patient's heart (e.g., within the LA or the RA), the capacitance value C varies based on the pressure within the heart, as is known to those of skill in the art. In other embodiments, the capacitor 202 can be or be part of a different type of capacitive sensor (e.g., a capacitive proximity sensor). In other embodiments, in addition to or in lieu of the capacitor 202, the device 200 may comprise one or more sensing elements configured to be implanted within the patient's heart and having an electrical parameter value that varies based on pressure within the heart. The sensing element(s), for example, may have a capacitance value that is variable based on pressure within the patient's heart (like capacitor 202), a resistance value that is variable based on pressure within the patient's heart, and/or another variable electrical perimeter value based on pressure within the patient's heart.

The device 200 also includes a sensing circuit 204 operably coupled to the capacitor 202. The sensing circuit 204 can be configured to be implanted within the patient's heart (e.g., within the LA or RA). For example, the sensing circuit 204 can be enclosed within a housing that is secured to a portion of the patient's heart (e.g., to the septal wall). The sensing circuit 204 can be located at the same portion of the patient's heart as the capacitor 202 and pressure sensor (e.g., within the same heart chamber), or can be located at a different portion (e.g., within a different heart chamber). Optionally, the capacitor 202, pressure sensor and/or sensing circuit 204 can be carried by a shunting element implanted in the patient's heart.

The capacitor 202 and sensing circuit 204 can be electrically coupled to each other by a switching assembly 206 (the coupling is depicted schematically in FIG. 2A as connection 207). The switching assembly 206 can include one or more switches, transistors, or any other structure suitable for selectively interconnecting electronic components to each other. The switching assembly 206 can also be carried by the shunting element (e.g., near the capacitor 202 and/or sensing circuit 204), or can be located at another region of the patient's heart. The switching assembly 206 can be contained within a housing (e.g., the same housing as the sensing circuit 204, or a different housing).

In some embodiments, the sensing circuit 204 is configured to measure the capacitance value C of the capacitor 202. The sensing circuit 204 can include electronic components configured to directly measure capacitance, as is known to those of skill in the art. For example, the sensing circuit 204 can include an oscillator or multivibrator circuit having a period proportional to the capacitance value C. In other embodiments, the sensing circuit 204 may be configured to measure one or more suitable electrical parameter values that vary based on pressure within the patient's heart. Optionally, the sensing circuit 204 can include or be coupled to a processor (not shown) configured to determine the intracardiac pressure (e.g., of the LA or the RA) based on the measured capacitance value C and/or electrical parameter value in accordance with techniques known to those of skill in the art. For example, the capacitance value C and pressure can have non-linear relationship, which can be implemented in a look-up table or other suitable data structure. The measured capacitance and/or pressure values can be transmitted to a device external to the patient's body (e.g., a controller, mobile device, etc.) via an antenna or other data transmission device implanted in the patient's body (not shown). In some embodiments, the measured capacitance and/or pressure values are used to adjust an implanted shunting element or another implanted or non-implanted medical device, as described in further detail below.

In some embodiments, the sensing circuit 204 includes active electronic components that use power from an implanted power source to operate (e.g., to measure the capacitance value C, store the capacitance measurements, calculate pressure values, transmit data, etc.). Accordingly, the device 200 can include a power circuit 208 electrically coupled to the sensing circuit 204 to provide power thereto. In the illustrated embodiment, for example, the power circuit 208 is electrically coupled to the sensing circuit 204 and also to an energy storage component 210 (e.g., a battery, a supercapacitor, a capacitor). The power circuit 208 can provide power to the energy storage component 210 and/or manage or otherwise regulate the power contained within the energy storage component 210. This energy can in turn be used to power to the sensing circuit 204 via the power circuit 208.

Although FIG. 2A illustrates a single energy storage component 210, in other embodiments the device 200 can include multiple energy storage components (e.g., two, three, four, five, or more). In other embodiments the energy storage component 210 can be omitted and the power circuit 208 can provide power directly to the sensing circuit 204. Additionally, although in the illustrated embodiment the sensing circuit 204, power circuit 208, and energy storage component 210 are coupled via to each other via connections separate from the switching assembly 206, in other embodiments some or all of these connections can be included in the switching assembly 206.

In some embodiments, the energy storage component 210 is adapted to receive energy (e.g., a chargeable battery, capacitor, a supercapacitor, or a combination thereof) such that the power circuit 208 is configured to charge the energy storage component 210. The use of a chargeable energy storage component 210 is expected to be advantageous in embodiments where the size of the energy storage component 210—and therefore, its energy density—is constrained by requirements for percutaneous delivery (e.g., no more than 0.5 cc volume) and/or by other requirements. In such embodiments, a wirelessly chargeable energy storage component may be capable of providing advantages (e.g., longer operational life) over a non-chargeable energy storage component.

The power circuit 208 and/or the energy storage component 210 can be configured to be implanted in the patient's heart (e.g., within the LA or RA). Optionally, the power circuit 208 and/or energy storage component 210 can each be enclosed within a housing that is secured to a portion of the patient's heart (e.g., to the septal wall). The power circuit 208 and/or energy storage component 210 can be located at the same portion of the patient's heart as the sensing circuit 204 (e.g., within the same heart chamber), or can be located at a different portion (e.g., a different heart chamber). In some embodiments, the power circuit 208 and/or energy storage component 210 are carried by an implantable shunting device or another medical device.

The power circuit 208 can be a wireless power circuit configured to wirelessly receive power from a source external to the patient's body (e.g., a wireless charging device—not shown). In such embodiments, the power circuit 208 can be operably coupled to an inductor 212 having an inductance value L. The power circuit 208 and inductor 212 can be electrically coupled to each other by the switching assembly 206 (the coupling is depicted schematically in FIG. 2A as connection 213). The inductor 212 can be a receiver coil or other structure configured for receiving power wirelessly, as is known to those of skill in the art. The inductor 212 can be configured to be implanted within a patient's heart (e.g., within the LA or RA and/or coupled to a septal wall, etc.). The power circuit 208 can receive power from the external source via the inductor 212 and can transmit the power for storage in the energy storage component 210 and/or to power the operation of the sensing circuit 204.

In some embodiments, the device 200 is intended to provide active sensing of intracardiac pressure via the capacitor 202 and sensing circuit 204. As such, during normal operation, the device 200 can be in the first configuration (e.g., an active sensing configuration), as illustrated in FIG. 2A. When in the first configuration, the device 200 can operate using power from an energy source internal to the patient (e.g., the energy storage component 210 and/or power circuit 208). The first configuration can also be the initial configuration of the device 200 when the device 200 is implanted in the patient's heart. The device 200 can be configured to remain in the first configuration unless an electronics failure or other malfunction occurs or is anticipated to occur. Alternatively or in combination, the device 200 can be configured to remain in the first configuration until prompted by a user to switch to the second configuration.

Referring next to FIG. 2B, the device 200 can switched to a second, different configuration (e.g., a passive sensing configuration) if active sensing is no longer desired or possible. When in the passive sensing configuration, the device 200 can function without using power from any implanted energy source (e.g., the energy storage component 210 and/or the power circuit 208). In some embodiments, the device 200 is switched to the second configuration if an electronics failure or other malfunction occurs that prevents the device 200 from performing active sensing and/or from drawing power from an implanted energy source. The electronics failure can include, for example, a failure or malfunction in one or more of the sensing circuit 204, the power circuit 208, the energy storage component 210, and/or another component of the device 200 (e.g., a processor, data transmission device, etc.—not shown). In some embodiments, the electronics failure includes a failure or malfunction in one or more of the following: wireless power receipt by the power circuit 208; transmission of power between the power circuit 208, the energy storage component 210, and/or the sensing circuit 204; charging of the energy storage component 210 by the power circuit 208; storage of energy in the energy storage component 210; transmission of power from the energy storage component 210 the sensing circuit 204; measurement of the capacitance value C by the sensing circuit 204; pressure determination by the sensing circuit 204 or by a processor; transmission of capacitance data and/or pressure data to an external device; and/or other failure modes. In other embodiments, the electronics failure is not a "failure" in the sense that the components of the device 200 are still operating as intended, but are nevertheless exhibiting a reduced ability to function (e.g., depletion of available energy in a non-chargeable energy storage component 210, loss of chargeability of a chargeable energy storage component 210 over multiple charge cycles, etc.).

When the device 200 is in the second configuration, the capacitor 202 can be electrically coupled to the inductor 212 in parallel to form a resonant circuit (e.g., an LC circuit). In some embodiments, the capacitor 202 and inductor 212 are electrically coupled to each other by the switching assembly 206 (the coupling is depicted schematically in FIG. 2B as connection 214). The characteristics of the resonant circuit can be determined based on the capacitance value C and the inductance value L. For example, the resonant frequency f of the resonant circuit can be governed by the following equation:

$$f = \frac{1}{2\pi\sqrt{LC}}$$

As a result, in the second configuration, the resonant frequency f of the resonant circuit varies based on the capacitance value C. The resonant frequency f can be measured by operably coupling an external device that can generate a time-varying magnetic field (not shown) to the resonant circuit, in accordance with techniques known to those of skill in the art. For example, a time-varying current can be applied using one or more coils of wires that are external and proximate to the patient's body. Given that the inductance value L is constant, the resonant frequency f measured by the external device can then be used to calculate the capacitance value C and therefore the corresponding pressure. Thus, even if the device 200 is no longer operating as an active sensing device (e.g., due to electronic malfunction or by user choice), the device 200 can still function as a passive sensing device with which intracardiac pressure values can be determined based on the resonant frequency f. Thus, the device 200 can still be used for pressure monitoring even if a failure or malfunction occurs in the components used for active sensing.

Optionally, when the device 200 is in the second configuration, the capacitor 202 can be electrically decoupled from the sensing circuit 204 and the inductor 212 can be electrically decoupled from the power circuit 208. As shown in FIG. 2B, the switching assembly 206 has decoupled the capacitor 202 from the sensing circuit 204 (as indicated by the omission of connection 207) and has decoupled the inductor 212 from the power circuit 208 (as indicated by the omission of connection 213). In such embodiments, the sensing circuit 204 does not measure the capacitance value C of the capacitor 202 and the power circuit 208 does not receive wireless power via the inductor 212. Instead, the capacitor 202 and inductor 212 can function as components of the resonant circuit. In such embodiments, the characteristics of the resonant circuit (e.g. the resonant frequency f) can be detected by a device external to the patient and used to calculate the corresponding pressure, thus allowing for passive sensing of intracardiac pressure.

Figure 3:
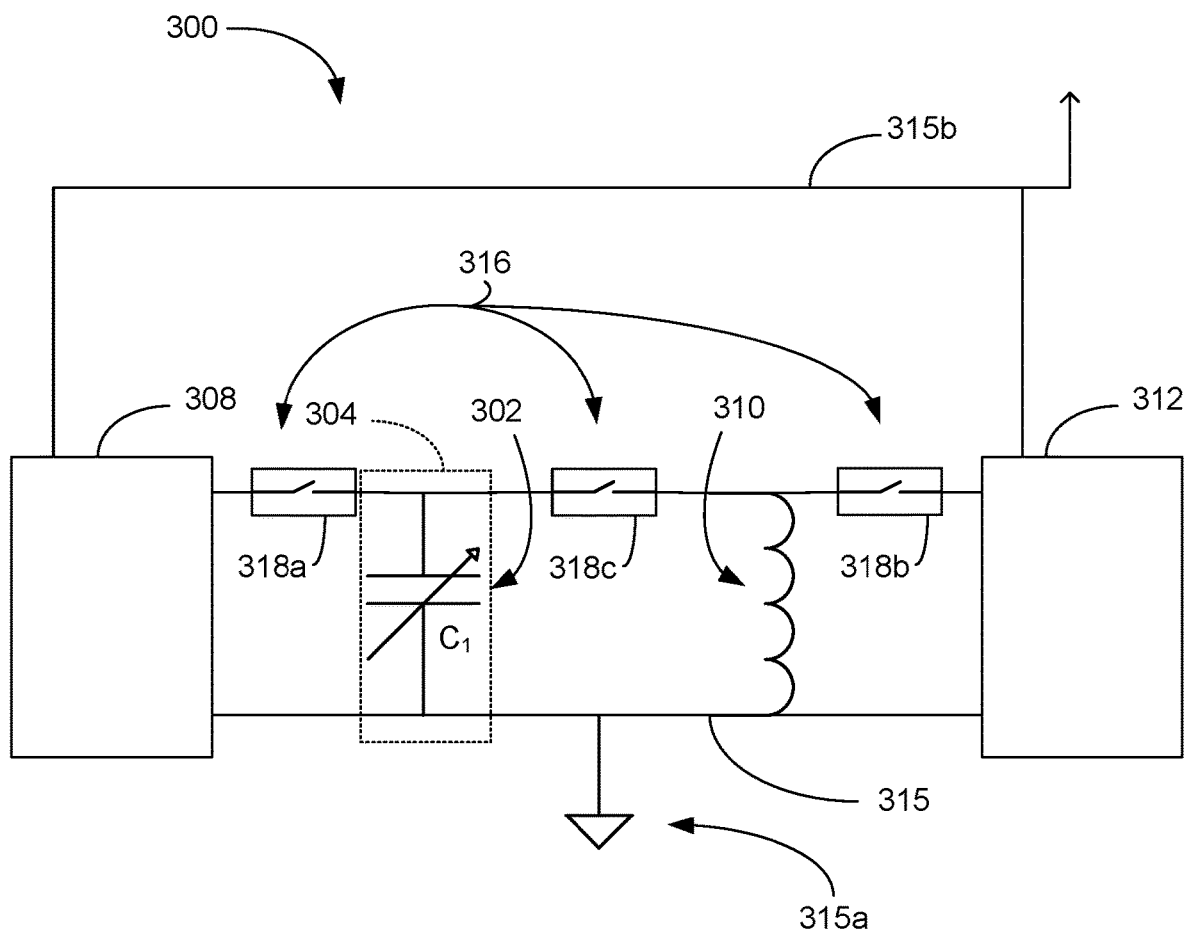
FIG. 3 is a circuit diagram of an intracardiac monitoring device configured in accordance with another embodiment of the present technology.

FIG. 3 is a circuit diagram of an intracardiac monitoring device 300 configured in accordance with another embodiment of the present technology. The components of the device 300 can be identical or generally similar to the corresponding components of the device 200 of FIGS. 2A and 2B. For example, the device 300 can include a capacitor 302 (e.g., a variable capacitor that is or is part of a capacitive pressure sensor 304 (shown schematically) operably coupled to a sensing circuit 308 (shown schematically) and an inductor 310 (e.g., a receiver coil) operably coupled to a power circuit 312 (shown schematically). Accordingly, the discussion of FIG. 3 will be limited to those features that differ from and/or were not described in detail with respect to the embodiment of FIGS. 2A and 2B.

As shown in FIG. 3, the capacitor 302, sensing circuit 308, inductor 310, and power circuit 312 can be arranged in parallel with each other, with the capacitor 302 and inductor 310 located between the sensing circuit 308 and power circuit 312. The capacitor 302, sensing circuit 308, inductor 310, and power circuit 312 can each be electrically coupled to a common potential 314 (e.g., ground) via wiring 315a and a power source (e.g., an energy storage component—not shown) via wiring 315b. The device 300 further includes a switching assembly 316 that electrically interconnects the capacitor 302, sensing circuit 308, inductor 310, and power circuit 312. In the illustrated embodiment, for example, the switching assembly 316 includes a first switch 318a between the capacitor 302 and the sensing circuit 308, a second switch 318b between the inductor 310 and the power circuit 312, and a third switch 318c between the capacitor 302 and the inductor 310. The switches 318a-c can be any electronic component capable of selectively opening and closing, such as one or more transistors (e.g., FETs, such as MOSFETs or JFETs).

When the device 300 is in an active sensing mode, the switching assembly 316 can be placed in a first configuration in which the first and second switches 318a-b are closed while the third switch 318c is open. As a result, the first switch 318a electrically couples the capacitor 302 to the sensing circuit 308 and the second switch 318b electrically couples the inductor 310 to the power circuit 312. The sensing circuit 308 and power circuit 312 are also electrically coupled via wiring 315. Thus, the power circuit 312 can provide power to the sensing circuit 308 (e.g., directly or indirectly via an implanted energy storage component (not shown)), and the sending circuit 308 can actively measure the capacitance value Ci of the capacitor 302 for pressure monitoring, as previously described. In the first configuration, because the third switch 318c is open, the capacitor 302 and inductor 310 are not electrically coupled in parallel. As a result, the inductor 310 is used solely for wirelessly receiving power, and does not form a resonant circuit with the capacitor 302.

To transition the device 300 into a passive sensing mode, the switching assembly 316 can be placed in a second configuration in which the first and second switches 318a-b are open while the third switch 318c is closed. As a result, the third switch 318c completes the circuit between the capacitor 302 and the inductor 310 so that these components are coupled in parallel to form a resonant circuit (e.g., an LC circuit). The resonant frequency of the resonant circuit can be measured externally from outside the patient's body to determine the capacitance value Ci of the capacitor 302 for pressure monitoring, as previously described. In the second configuration, the open state of the first and second switches 318a-b can result in the sensing circuit 308 being electrically decoupled from the capacitor 302 and the power circuit 312 being electrically decoupled from the inductor 310.

In some embodiments, the switching assembly 316 is configured to automatically transition from the first configuration (e.g., the active sensing mode) to the second configuration (e.g., the passive sensing mode) in response to an electronics failure or other malfunction (e.g., in the sensing circuit 308, power circuit 312, an energy storage component, etc.). For example, when there is a loss of power in the device (e.g., the voltage at the switches 318a-c goes to zero), the first and second switches 318a-b can automatically switch from a closed state to an open state, while the third switch 318c can automatically switch from an open state to a closed state. The automatic switching can be implemented in a number of different ways known to those of skill in the art. For example, the first and second switches 318a-b can be p-channel enhancement mode FETs (which are off when gate drive is absent) and the third switch 318c can be an re-channel depletion mode FET (which is on when gate drive is absent).

Alternatively or in combination, the switching assembly 316 can be configured to transition from the first configuration to the second configuration in response to a control signal (e.g., transmitted from another component of the device 300 or from a controller external to the patient's body). In some embodiments, the control signal is transmitted to the switching assembly 316 after an electronics failure or malfunction has occurred. In other embodiments, however, the control signal is transmitted before an electronics failure or malfunction has occurred. For example, if one or more components of the device 300 (e.g., the sensing circuit 308, power circuit 312, an implanted energy storage component, etc.) are anticipated to fail or malfunction, the switching assembly 316 can be proactively transitioned to the second configuration before the failure or malfunction actually occurs in order to avoid interruptions in the operation of the device 300. Optionally, the switching assembly 316 can be proactively transitioned to the second configuration even if a failure or malfunction is not anticipated, as described in greater detail below.

In some embodiments, a clinician can determine (e.g., based on previous experience, historical data of the device 300, and/or data received from the device 300) that one or more components of the device 300 have failed or malfunctioned, are expected to fail or malfunction, or are otherwise not capable of operating in an active sensing mode (e.g., a chargeable energy storage component is nearing or past the maximum manufacturer-recommended number of charge cycles). The clinician can use a controller to wirelessly transmit a signal to the switching assembly 316 to transition it into the second configuration for passive sensing. In another example, the device 300 can include an internal controller for monitoring the state of various components (e.g., the sensing circuit 308, power circuit 312, an energy storage component, etc.). If the internal controller detects that the component(s) have failed or malfunctioned, are about to fail or malfunction, or are otherwise not capable of operating in an active sensing mode, the internal controller can signal the switching assembly 316 to transition into the second configuration for passive sensing.

Optionally, the device 300 can be switched into the passive sensing mode even if no failure or malfunction has occurred or is expected to occur. Switching to passive sensing can be beneficial, for example, to reduce energy consumption of the device 300 and/or to allow for redundancy in pressure monitoring techniques to confirm that the device 300 is functioning properly. As described above, the switching can be performed automatically or in response to a control signal from another device component or from an external controller. In some embodiments, the switching is temporary and the device 300 can be subsequently switched back into the active sensing mode, e.g., if energy consumption is no longer an issue, once passive measurements are no longer desired, after a set period of time, after completion of a task, and/or another criteria has been met. Optionally, the device 300 can be cycled between the active and passive sensing modes multiple times, e.g., as necessary or appropriate for patient monitoring and treatment.

Figure 4:
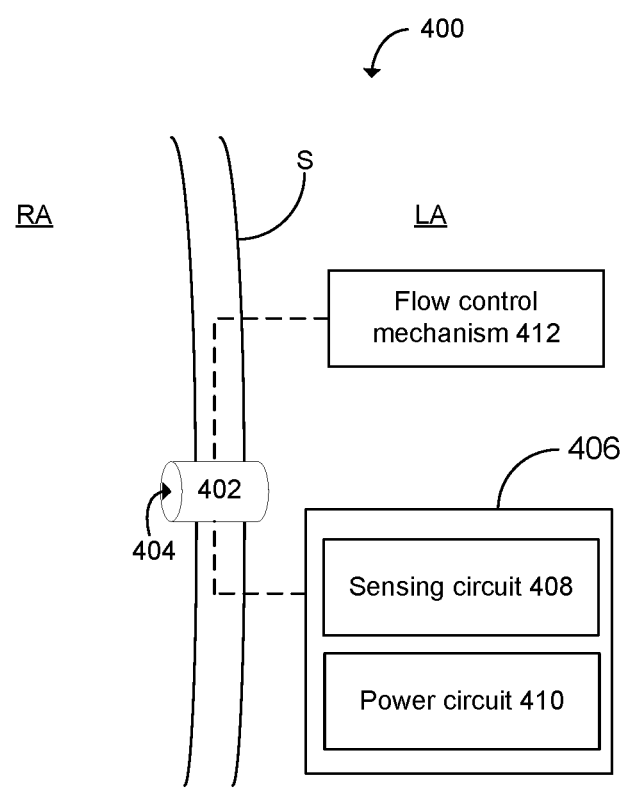
FIG. 4 is a schematic illustration of an interatrial shunting system configured in accordance with an embodiment of the present technology.

FIG. 4 is a schematic illustration of an interatrial shunting system 400 configured in accordance with an embodiment of the present technology. The system 400 includes a shunting element 402 defining a lumen 404 therethrough. When implanted in the septal wall S, the system 400 can fluidly connect the left atrium LA and the right atrium RA via the lumen 404. The system 400 can include an intracardiac monitoring device 406 generally similar or identical to the devices described herein (e.g., device 200 of FIGS. 2A-2B or device 300 of FIG. 3). For example, the device 406 can include a sensing circuit 408 and power circuit 410 configured for switching between active and passive sensing modes, as previously described.

The device 406 can be implanted in a patient's heart prior to, concurrently with, or after implantation of the shunting element 402. For example, in some embodiments, the device 406 is implanted first and is used to monitor intracardiac pressure for a period of time (e.g., days, weeks, months, etc.) to determine whether the patient would benefit from an interatrial shunt. If the clinician determines that an interatrial shunt would be beneficial, the shunting element 402 can subsequently be implanted. Optionally, the pressure data generated by the device 406 can be used to determine other treatment parameters, such as the geometry (e.g., size and/or shape) of the shunting element 402. After implantation of the shunting element 402, the device 406 can be used to continue monitoring intracardiac pressure, e.g., to assess performance of the shunting element 402, to determine whether adjustments to the shunting element 402 would be beneficial, etc.

In some embodiments, the shunting element 402 is selectively adjustable after implantation to control blood flow between the LA and RA based on pressure data generated by the device 406 and/or based upon other data or attributes of the patient's health. For example, the device 406 can be used to measure pressure in one or more heart chambers over time, and adjustments to the shunting element 402 can be made in response to changes in the measured pressure (e.g., increasing or decreasing pressure over time). As another example, pressure measurements from the device 406 can be used to calculate a pressure differential between different heart chambers (e.g., the LA and the RA), and adjustments to the shunting element 402 can be made in response to the calculated pressure differential (e.g., whether the pressure differential is greater than or less than a predetermined threshold, whether the pressure differential exceeds a predetermined range, etc.). In yet another example, adjustments to the shunting element 402 can be made based on factors unrelated to the sensor(s) or the intracardiac pressure.

In some embodiments, the interatrial shunting system 400 includes a flow control mechanism 412 configured to adjust the shunting element 402 (e.g., in a non-invasive manner). The flow control mechanism 412 can change a shape or other characteristic of the shunting element 402 to change the flow of fluid through the lumen 404. In some embodiments, the flow control mechanism 412 selectively changes the geometry (e.g., size and/or shape) of the lumen 404 to change the flow resistance through the lumen 404. For example, the flow control mechanism 412 can be configured to selectively increase a diameter of the lumen 404 and/or selectively decrease a diameter of the lumen 404.

Alternatively or in combination, the shunting element 402 can be adjusted by a clinician via a suitable adjustment device. For example, in some embodiments, the shunting element 402 is a balloon-expandable stent having an adjustable lumen 404 diameter (e.g., adjustable within a range from 5 mm to 12 mm). If the clinician determines that an adjustment would be beneficial (e.g., considering data generated by one or more pressure sensors, if the patient's disease progresses, if the shunting element 402 narrows or otherwise becomes obstructed), the clinician can use a balloon catheter or similar adjustment device to adjust (e.g., expand or contract) the diameter of the lumen 404 of the shunting element 402. In some embodiments, the shunting element 402 and/or adjustment device include a radiopaque material, such that the adjustment procedure can be performed under fluoroscopic guidance.

In some embodiments, the size and/or shape of the lumen 404 can be adjusted on a consistent time schedule (e.g., continuously, hourly, daily, monthly, yearly, etc.). Consistent adjustments might be made, for example, to adjust the flow of blood based on an exertion level and/or heart rate of the patient, which changes frequently over the course of a day. For example, the system 400 can have a baseline state in which the lumen 404 is substantially closed and does not allow substantial blood flow between the LA and RA, and an active state in which the lumen 404 is open and allows blood to flow between the LA and RA. The system 400 can transform from the baseline state to the active state whenever the exertion level and/or heart rate of the patient increases due to exercise, stress, or other factors. As another example, consistent adjustments can be made based on, or in response to, sensed physiological parameters, including, for example, sensed left atrial pressure and/or right atrial pressure. If the left atrial pressure increases, the system 400 can automatically increase a diameter of the lumen 404 to increase blood flow between the LA and the RA. In yet another example, the system 400 can be configured to adjust based on, or in response to, an input parameter from another device such as a pulmonary arterial pressure sensor, insertable cardiac monitor, pacemaker, defibrillator, cardioverter, wearable, external ECG or PPG, and the like.

Some embodiments of the present technology adjust the relative size and/or shape of the lumen 404 only after a threshold has been reached (e.g., a sufficient period of time has elapsed). This may be done, for example, to avoid unnecessary back and forth adjustments and/or avoid changes based on clinically insignificant changes in patient condition. In some embodiments, adjustments may occur occasionally as a patient's condition changes. For example, the lumen 404 may gradually open if a patient experiences a sustained rise in left atrial pressure (e.g., rate of change is above a predetermined threshold, and/or the left atrial pressure remains higher than a predetermined threshold for longer than a predetermined amount of time), pulmonary artery pressure, weight, or another physiologically relevant parameter. Alternatively or in combination, adjustments can occur if pressure exceeds a threshold or increases by a threshold amount over a period of time (e.g., several days or more). The diameter of the lumen 404 can then be altered to change the degree of blood flow between the LA and RA and to avoid decompensation and/or generally improve patient status.

The system 400 can also enable a clinician to periodically (e.g., monthly, bi-monthly, annually, as needed, etc.) adjust the geometry of the lumen 404 to improve patient outcomes. For example, during a patient visit, the clinician can assess a number of patient parameters and determine whether adjusting the geometry of the lumen 404, and thus altering blood flow between the LA and the RA, would provide better treatment and/or enhance the patient's quality of life. Patient parameters can include, for example, physiological parameters (e.g., left atrial blood pressure, right atrial blood pressure, the difference between left and right atrial blood pressures, flow velocity, heart rate, cardiac output, myocardial strain, etc.), subjective parameters (e.g., whether the patient is fatigued, how the patient feels during exercise, etc.), and other parameters known in the art for assessing whether a treatment for HF is working.

In some system embodiments, multiple pressure sensors can be employed (e.g., sensors positioned in different anatomical locations such as in the LA and in the RA). In such embodiments, the plurality of sensors could be configured identically, or the configurations can differ among sensors. For example, some sensors can be operational in an active mode (e.g., driven by a power source internal to the patient) while others may be operational in a passive, resonant mode as described herein. In some embodiments containing a plurality of sensors, some sensors can be configured to toggle between passive and active operational modes, and others can be fixed permanently for use in a single mode of operation.

In many of the embodiments described herein, the disclosed systems include capacitors that are pressure sensors or are parts of capacitive pressure sensors. However, one skilled in the art will recognize that systems configured in accordance with the present technology can be modified to accommodate the use of other suitable sensors for measuring pressure (e.g., a piezoresistive type sensor). For example, in another embodiment, four piezoresistive elements can be diffused into a semiconductor diaphragm fabricated as part of a hermetic volume at a reference pressure and electronic circuitry known to one skilled in the art utilized to measure the change in resistances resulting from the change in pressure on said diaphragm. In another embodiment, the four resistive elements can be piezoresistive materials deposited on the surface of the diaphragm. In still another embodiment, two piezoresistive elements can be diffused into a semiconductor diaphragm fabricated as part of a hermetic volume at a reference pressure, and electronic circuitry known to one skilled in the art utilized to measure the change in the resistances resulting from the change in pressure on said diaphragm. In another embodiment, the two resistive elements can be piezoresistive materials deposited on the surface of the diaphragm. In yet another embodiment, one piezoresistive element can be diffused into semiconductor diaphragm fabricated as part of a hermetic volume at a reference pressure, and electronic circuitry known to one skilled in the art utilized to measure the change in resistances resulting from the change in pressure on said diaphragm. In other embodiments, the resistive element can be piezoresistive materials deposited on the surface of the diaphragm. Those skilled in the art will recognize that a different number of piezoresistive elements can be utilized in additional embodiments similar to those described above, and that other types of pressure sensitive components can be substituted for the piezoresistive elements with only minor corresponding changes.

Some examples of the systems described herein may utilize combinations of sensing technologies. For example, a system configured in accordance with the present technology may include both a capacitor/capacitive sensor as well as a non-capacitive pressure sensor. In an example configuration, the non-capacitive sensor could be enabled to operate when the system is in an active configuration (e.g., driven by power from a power circuit and/or an energy storage component) and the capacitor/capacitive sensor could be enabled to operate when the system is in a passive configuration (e.g., not driven by power from a power circuit and/or an energy storage component). As described herein, switching circuitry can be utilized to toggle back and forth between each configuration. Such a design is expected to increase the robustness of the system, and can be useful to ensure the accuracy of the pressure measurements taken by the system (e.g., by periodically taking and comparing measurements in both active/passive configurations). In some embodiments, the capacitive and non-capacitive systems may utilize the same diaphragm. For example, one, two, or four piezoresistive elements could be deposited or screen-printed on, diffused into, or otherwise functionally-coupled to the flexible capacitor electrode.

As one of skill in the art will appreciate from the disclosure herein, various components of the intracardiac monitoring devices described above can be omitted without deviating from the scope of the present technology. Likewise, additional components not explicitly described above may be added to the intracardiac pressure monitoring devices without deviating from the scope of the present technology. Accordingly, the devices and systems described herein are not limited to those configurations expressly identified, but rather encompasses variations and alterations of the described devices and systems.

Examples

Several aspects of the present technology are set forth in the following examples:

1. A device for monitoring pressure within a patient's heart, the device comprising:
    a capacitor positionable within the patient's heart and having a capacitance value that is variable based on pressure within the patient's heart;
    a sensing circuit operably coupled to the capacitor and configured to measure the capacitance value thereof;
    an inductor positionable within the patient's heart;
    a power circuit operably coupled to the inductor and configured to wirelessly receive power from a source external to the patient's body via the inductor, wherein the power circuit is electrically coupled to the sensing circuit to provide power thereto; and
    a switching assembly, wherein—
        when the switching assembly is in a first configuration, the switching assembly electrically couples the capacitor to the sensing circuit and electrically couples the inductor to the power circuit, and
        when the switching assembly is in a second configuration, the switching assembly electrically couples the capacitor to the inductor to form a resonant circuit, wherein a resonant frequency of the resonant circuit varies based on the capacitance value of the capacitor.

2. The device of example 1 wherein, when the switching assembly is in the second configuration, the capacitor is electrically decoupled from the sensing circuit and the inductor is electrically decoupled from the power circuit.

3. The device of example 1 or example 2 wherein the switching assembly is configured to transition between the first configuration and the second configuration in response to an electronics failure in the device.

4. The device of example 3 wherein the electronics failure comprises a malfunction in power transmission from the power circuit to the sensing circuit.

5. The device of example 3 or example 4, further comprising an energy storage component electrically coupled to the sensing circuit to provide power thereto, wherein the power circuit is electrically coupled to the energy storage component to charge the energy storage component.

6. The device of example 5 wherein the electronics failure comprises a malfunction in power transmission from the energy storage component to the sensing circuit.

7. The device of example 5 wherein the electronics failure comprises a malfunction in charging of the energy storage component by the power circuit.

8. The device of any one of examples 1-7 wherein the switching assembly comprises one or more MOSFETs.

9. The device of example 8 wherein the switching assembly comprises:
    a first switch configured to electrically couple the capacitor to the sensing circuit;
    a second switch configured to electrically couple the inductor to the power circuit; and
    a third switch configured to electrically couple the capacitor to the inductor.

10. The device of example 9 wherein:
    when the switching assembly is in the first configuration, the first and second switches are closed, and the third switch is open; and
    when the switching assembly is in the second configuration, the first and second switches are open, and the third switch is closed.

11. The device of any one of examples 1-10 wherein the capacitance value is variable based on one or more of the following: a left atrial pressure, a right atrial pressure, a left ventricular pressure, a right ventricular pressure, a pulmonary artery pressure, a vena cava pressure, and a coronary sinus pressure.

12. The device of any one of examples 1-11 wherein the sensing circuit is configured to measure the capacitance value continuously, intermittently, and/or in response to an event.

13. A device for monitoring pressure within a patient's heart, the device comprising:
    a capacitive pressure sensor positionable within the patient's heart and including a variable capacitor having a capacitance value that is variable based on the pressure within the patient's heart;
    a sensing circuit positionable within the patient's heart and operably coupled to the capacitive pressure sensor via a first switch, wherein the sensing circuit is configured to measure the capacitance value of the variable capacitor of the capacitive pressure sensor;
    an inductive receiver coil positionable within the patient's heart;
    a power circuit positionable within the patient's heart and operably coupled to the inductive receiver coil via a second switch, wherein the power circuit is configured to wirelessly receive power from a source external to the patient's body via the inductive receiver coil, and wherein the power circuit is electrically coupled to the sensing circuit to provide power thereto; and
    a third switch operably coupling the variable capacitor to the inductive receiver coil,
    wherein— when the device is in an initial state, the first switch electrically couples the capacitive pressure sensor to the sensing circuit and the second switch electrically couples the inductive receiver coil to the power circuit, and when an electronics failure occurs in the device, the third switch electrically couples the variable capacitor in parallel with the inductive receiver coil to form a resonant LC circuit, wherein a resonant frequency of the resonant LC circuit varies based on the capacitance value of the variable capacitor.

14. The device of example 13 wherein the electronics failure comprises a malfunction in power transmission from the power circuit to the sensing circuit.

15. The device of example 13 wherein the electronics failure comprises a failure or malfunction in one or more of the following: wireless power receipt by the power circuit, measurement of the capacitance value by the sensing circuit, pressure determination by the sensing circuit or by a processor, and transmission of capacitance data and/or pressure data to a device external to the patient.

16. The device of any one of examples 13-15, further comprising an energy storage component electrically coupled to the sensing circuit to provide power thereto, wherein the power circuit is electrically coupled to the energy storage component to charge the energy storage component.

17. The device of example 16 wherein the electronics failure comprises a malfunction in power transmission from the energy storage component to the sensing circuit.

18. The device of example 16 wherein the electronics failure comprises a malfunction in charging of the energy storage component by the power circuit.

19. The device of any one of examples 13-18 wherein at least one of the switches comprises a MOSFET.

20. The device of any one of examples 13-19 wherein the capacitance value is variable based on one or more of the following: a left atrial pressure, a right atrial pressure, a left ventricular pressure, a right ventricular pressure, a pulmonary artery pressure, a vena cava pressure, and a coronary sinus pressure.

21. The device of any one of examples 13-20 wherein the sensing circuit is configured to measure the capacitance value continuously, intermittently, and/or in response to an event.

22. A system for shunting blood between cavities of a patient's heart, the system comprising:
a shunting element having a lumen extending therethrough, wherein, when the shunting element is implanted in the patient, the lumen is configured to fluidly couple the cavities of the patient's heart; and
the device for monitoring pressure of any one of examples 1-21.

23. A system for shunting fluid between a first body region of a patient and a second body region of the patient, the system comprising:
a shunting element having a lumen extending therethrough, wherein, when the shunting element is implanted in the patient, the lumen is configured to fluidly couple the first body region and the second body region; and
the device for monitoring pressure of any one of examples 1-21.

24. A method of monitoring pressure within a patient's heart, the method comprising:
electrically coupling an implanted inductor to an implanted power circuit via a first switch, wherein the implanted power circuit is configured to receive power from an external source via the implanted inductor;
electrically coupling an implanted capacitor to an implanted sensing circuit via a second switch, wherein the implanted sensing circuit is configured to measure a capacitance value of the implanted capacitor while receiving power from the implanted power circuit; and
electrically coupling the implanted inductor and the implanted capacitor via a third switch to form a resonant circuit, wherein a resonant frequency of the resonant circuit varies based on the capacitance value of the capacitor.

25. The method of example 24, further comprising:
electrically decoupling the implanted inductor and the implanted power circuit via the first switch; and
electrically decoupling the implanted capacitor and the implanted sensing circuit via the second switch.

26. A method of monitoring pressure within a patient's heart using an implanted capacitor, the method comprising:
measuring a capacitance value of the implanted capacitor using an implanted sensing circuit;
electrically coupling an implanted inductor and the implanted capacitor to form a resonant circuit, wherein a resonant frequency of the resonant circuit varies based on the capacitance value of the capacitor; and
measuring the resonant frequency of the resonant circuit using a device external to the patient.

27. The method of example 26 wherein the capacitance value of the implanted capacitor varies based on pressure within the patient's heart.

28. The method of example 26 or example 27 wherein the implanted capacitor is initially electrically coupled to the implanted sensing circuit, and the implanted inductor is initially electrically coupled to an implanted power circuit.

29. The method of example 28 further comprising:
wirelessly receiving power at the implanted power circuit via the implanted inductor;
transmitting power from the implanted power circuit to the implanted sensing circuit.

30. The method of example 29, further comprising:
charging an implanted energy storage component via the power received by the implanted power circuit; and
transmitting power from the implanted energy storage component to the implanted sensing circuit.

31. The method of any one of examples 28-30 wherein electrically coupling the implanted inductor and the implanted capacitor further comprises:
electrically decoupling the implanted inductor from the implanted power circuit; and
electrically decoupling the implanted capacitor from the implanted sensing circuit.

32. The method of any one of examples 28-31 wherein the implanted inductor and implanted capacitor are electrically coupled to each other automatically in response to an electronics failure.

33. The method of any one of examples 28-31, further comprising:
in response to a control signal from a controller external to the patient, electrically coupling the implanted inductor and implanted capacitor to each other.

34. The method of any one of examples 26-33 wherein measuring the resonant frequency comprises applying a magnetic field to the implanted inductor using the device external to the patient.

35. The method of any one of examples 26-34, further comprising:

determining a first pressure within the patient's heart based on the capacitance value measured by the sensing circuit; and determining a second pressure within the patient's heart based on the resonant frequency measured by a device external to the patient.

36. The method of example 35, further comprising adjusting a shunting element implanted in the patient's heart based, at least in part, on the first pressure or the second pressure.

37. A device for monitoring pressure within a heart of a patient, the device comprising:
   a first element positionable within the heart of the patient, wherein the first element comprises an electrical parameter value that varies based on pressure within the heart;
   a sensing circuit operably coupled to the first element and configured to measure the electrical parameter value thereof;
   a second element positionable within the heart, where said second element is configured for wirelessly receiving power;
   a power circuit operably coupled to the second element and configured to wirelessly receive power from a source external to the patient via the second element, wherein the power circuit is electrically coupled to the sensing circuit to provide power thereto; and
   a switching assembly, wherein—
      when the switching assembly is in a first configuration, the switching assembly electrically couples the first element to the sensing circuit and electrically couples the second element to the power circuit, and
      when the switching assembly is in a second configuration, the switching assembly electrically couples the first element to the second element to form a resonant system, wherein a resonant frequency of the resonant system varies based on the electrical parameter value of the first element.

38. A device for monitoring pressure within a patient's heart, the device comprising:
   a first pressure sensing element positionable within the patient's heart, wherein the first pressure sensing element comprises a capacitor and having a capacitance value that varies based on pressure within the patient's heart;
   a second pressure sensing element positionable within the patient's heart, wherein the second pressure sensing element comprises a resistance value that varies based on pressure within the patient's heart;
   a first sensing circuit operably coupled to the first pressure sensing element and configured to measure the capacitance value thereof;
   a second sensing circuit operably coupled to the second pressure sensing element and configured to measure the resistance value thereof;
   an inductor positionable within the patient's heart;
   a power circuit operably coupled to the inductor and configured to wirelessly receive power from a source external to the patient's body via the inductor, wherein the power circuit is electrically coupled to the first and second sensing circuits to provide power thereto; and
   a switching assembly, wherein—
      when the switching assembly is in a first configuration, the switching assembly electrically couples the second pressure sensing element to the second sensing circuit and electrically couples the inductor to the power circuit, and
      when the switching assembly is in a second configuration, the switching assembly electrically couples the capacitor to the inductor to form a resonant circuit, and wherein a resonant frequency of the resonant circuit varies based on the capacitance value of the capacitor.

39. A device for monitoring pressure within a heart of a patient, the device comprising:
   a plurality of sensing elements positionable within the heart of the patient, wherein the individual sensing elements comprise an electrical parameter value that is variable based on pressure within the heart;
   a sensing circuit operably coupled to said pressure sensing elements and configured to measure pressure-variable electrical parameters thereof;
   a power receiving element positionable within the patient's heart;
   a power circuit operably coupled to power receiving element and configured to wirelessly receive power, via the power receiving element, from a source external to the patient, wherein the power circuit is electrically coupled to the sensing circuit to provide power thereto; and
   a switching assembly, wherein—
      when the switching assembly is in a first configuration, the switching assembly electrically couples one or more of the pressure sensing elements to the sensing circuit and electrically couples the power receiving element to the power circuit, and
      when the switching assembly is in a second configuration, the switching assembly electrically couples one pressure sensing element to the power receiving element to form a resonant circuit, and wherein a resonant frequency of the resonant circuit varies based on the pressure-variable parameter of the pressure sensing element.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

Embodiments of the present disclosure may be implemented as computer-executable instructions, such as routines executed by a general-purpose computer, a personal computer, a server, or other computing system. The present technology can also be embodied in a special purpose computer or data processor that is specifically programmed, configured, or constructed to perform one or more of the computer-executable instructions explained in detail herein. The terms "computer" and "computing device," as used generally herein, refer to devices that have a processor and non-transitory memory, as well as any data processor or any device capable of communicating with a network. Data processors include programmable general-purpose or special-purpose microprocessors, programmable controllers, ASICs, programming logic devices (PLDs), or the like, or a combination of such devices. Computer-executable instructions may be stored in memory, such as RAM, ROM, flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the LA and RA, the LV and the right ventricle (RV), or the LA and the coronary sinus, it should be appreciated that similar embodiments could be utilized for shunts between other chambers of heart or for shunts in other regions of the body.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for monitoring pressure within a patient's heart, the device comprising:
    a capacitor positionable within the patient's heart and having a capacitance value that is variable based on pressure within the patient's heart;
    a sensing circuit operably coupled to the capacitor and configured to measure the capacitance value thereof;
    an inductor positionable within the patient's heart;
    a power circuit operably coupled to the inductor and configured to wirelessly receive power from a source external to the patient's body via the inductor, wherein the power circuit is electrically coupled to the sensing circuit to provide power thereto; and
    a switching assembly, wherein—
        when the switching assembly is in a first configuration, the switching assembly electrically couples the capacitor to the sensing circuit and electrically couples the inductor to the power circuit, and
        when the switching assembly is in a second configuration, the switching assembly electrically couples the capacitor to the inductor to form a resonant circuit, wherein a resonant frequency of the resonant circuit varies based on the capacitance value of the capacitor.

2. The device of claim 1 wherein, when the switching assembly is in the second configuration, the capacitor is electrically decoupled from the sensing circuit and the inductor is electrically decoupled from the power circuit.

3. The device of claim 1 wherein the switching assembly is configured to transition between the first configuration and the second configuration in response to an electronics failure in the device.

4. The device of claim 3 wherein the electronics failure comprises a malfunction in power transmission from the power circuit to the sensing circuit.

5. The device of claim 3, further comprising an energy storage component electrically coupled to the sensing circuit to provide power thereto, wherein the power circuit is electrically coupled to the energy storage component to charge the energy storage component.

6. The device of claim 5 wherein the electronics failure comprises a malfunction in power transmission from the energy storage component to the sensing circuit.

7. The device of claim 5 wherein the electronics failure comprises a malfunction in charging of the energy storage component by the power circuit.

8. The device of claim 1 wherein the switching assembly comprises one or more MOSFETs.

9. The device of claim 8 wherein the switching assembly comprises:
- a first switch configured to electrically couple the capacitor to the sensing circuit;
- a second switch configured to electrically couple the inductor to the power circuit; and
- a third switch configured to electrically couple the capacitor to the inductor.

10. The device of claim 9 wherein:
- when the switching assembly is in the first configuration, the first and second switches are closed, and the third switch is open; and
- when the switching assembly is in the second configuration, the first and second switches are open, and the third switch is closed.

11. The device of claim 1 wherein the capacitance value is variable based on one or more of the following: a left atrial pressure, a right atrial pressure, a left ventricular pressure, a right ventricular pressure, a pulmonary artery pressure, a vena cava pressure, and a coronary sinus pressure.

12. The device of claim 1 wherein the sensing circuit is configured to measure the capacitance value continuously, intermittently, and/or in response to an event.

13. A device for monitoring pressure within a patient's heart, the device comprising:
- a capacitive pressure sensor positionable within the patient's heart and including a variable capacitor having a capacitance value that is variable based on the pressure within the patient's heart;
- a sensing circuit positionable within the patient's heart and operably coupled to the capacitive pressure sensor via a first switch, wherein the sensing circuit is configured to measure the capacitance value of the variable capacitor of the capacitive pressure sensor;
- an inductive receiver coil positionable within the patient's heart;
- a power circuit positionable within the patient's heart and operably coupled to the inductive receiver coil via a second switch, wherein the power circuit is configured to wirelessly receive power from a source external to the patient's body via the inductive receiver coil, and wherein the power circuit is electrically coupled to the sensing circuit to provide power thereto; and
- a third switch operably coupling the variable capacitor to the inductive receiver coil, wherein—
- when the device is in an initial state, the first switch electrically couples the capacitive pressure sensor to the sensing circuit and the second switch electrically couples the inductive receiver coil to the power circuit, and
- when an electronics failure occurs in the device, the third switch electrically couples the variable capacitor in parallel with the inductive receiver coil to form a resonant LC circuit, wherein a resonant frequency of the resonant LC circuit varies based on the capacitance value of the variable capacitor.

14. The device of claim 13 wherein the electronics failure comprises a malfunction in power transmission from the power circuit to the sensing circuit.

15. The device of claim 13 wherein the electronics failure comprises a failure or malfunction in one or more of the following: wireless power receipt by the power circuit, measurement of the capacitance value by the sensing circuit, pressure determination by the sensing circuit or by a processor, and transmission of capacitance data and/or pressure data to a device external to the patient.

16. The device of claim 13, further comprising an energy storage component electrically coupled to the sensing circuit to provide power thereto, wherein the power circuit is electrically coupled to the energy storage component to charge the energy storage component.

17. The device of claim 16 wherein the electronics failure comprises a malfunction in power transmission from the energy storage component to the sensing circuit.

18. The device of claim 16 wherein the electronics failure comprises a malfunction in charging of the energy storage component by the power circuit.

19. The device of claim 13 wherein at least one of the switches comprises a MOSFET.

20. The device of claim 13 wherein the capacitance value is variable based on one or more of the following: a left atrial pressure, a right atrial pressure, a left ventricular pressure, a right ventricular pressure, a pulmonary artery pressure, a vena cava pressure, and a coronary sinus pressure.

21. The device of claim 13 wherein the sensing circuit is configured to measure the capacitance value continuously, intermittently, and/or in response to an event.

22. A device for monitoring pressure within a heart of a patient, the device comprising:
- a first element positionable within the heart of the patient, wherein the first element comprises an electrical parameter value that varies based on pressure within the heart;
- a sensing circuit operably coupled to the first element and configured to measure the electrical parameter value thereof;
- a second element positionable within the heart, where said second element is configured for wirelessly receiving power;
- a power circuit operably coupled to the second element and configured to wirelessly receive power from a source external to the patient via the second element, wherein the power circuit is electrically coupled to the sensing circuit to provide power thereto; and
- a switching assembly, wherein—
  - when the switching assembly is in a first configuration, the switching assembly electrically couples the first element to the sensing circuit and electrically couples the second element to the power circuit, and
  - when the switching assembly is in a second configuration, the switching assembly electrically couples the first element to the second element to form a resonant system, wherein a resonant frequency of the resonant system varies based on the electrical parameter value of the first element.

* * * * *